(12) United States Patent
Miyagi

(10) Patent No.: US 6,461,330 B1
(45) Date of Patent: Oct. 8, 2002

(54) SURGICAL OPERATION GUIDING APPARATUS

(75) Inventor: Kunihiko Miyagi, Tokyo (JP)

(73) Assignee: Machida Endoscope Co., Ltd. (JP)

( * ) Notice: Subject to any disclaimer, the term of this patent is extended or adjusted under 35 U.S.C. 154(b) by 188 days.

(21) Appl. No.: 09/585,847

(22) Filed: Jun. 1, 2000

(51) Int. Cl.[7] ............................................. A61M 5/00
(52) U.S. Cl. .................... 604/117; 604/158; 604/164.01
(58) Field of Search ........................... 604/117, 164.01, 604/164.04, 523, 533, 534, 535, 536

(56) References Cited

U.S. PATENT DOCUMENTS

| | | | |
|---|---|---|---|
| 3,750,667 A | * 8/1973 | Pshenichny et al. | ........ 604/117 |
| 4,593,681 A | 6/1986 | Soni | |
| 5,141,496 A | * 8/1992 | Dalto et al. | .................. 604/117 |
| 5,183,465 A | * 2/1993 | Xanthakos et al. | .......... 604/106 |
| 5,241,969 A | * 9/1993 | Carson et al. | ............... 600/566 |
| 5,320,608 A | * 6/1994 | Gerrone | ....................... 604/117 |
| 5,364,365 A | 11/1994 | Wortrich | |
| 5,366,446 A | 11/1994 | Tal et al. | |
| 5,370,625 A | 12/1994 | Shichman | |
| 5,456,673 A | 10/1995 | Ziegler et al. | |
| 5,569,290 A | 10/1996 | McAfee | |
| 5,792,112 A | 8/1998 | Hart et al. | |
| 6,117,143 A | * 9/2000 | Hynes et al. | ................ 600/429 |
| 6,200,291 B1 | * 3/2001 | Di Pietro | ..................... 604/117 |
| 6,213,977 B1 | * 4/2001 | Hjertman et al. | ........... 604/117 |
| 6,315,760 B1 | * 11/2001 | Sharp | ......................... 604/189 |

FOREIGN PATENT DOCUMENTS

JP    Hie-9-154803    6/1997

* cited by examiner

*Primary Examiner*—Teresa Walberg
*Assistant Examiner*—Vinod D Patel
(74) *Attorney, Agent, or Firm*—Eugene Stephens & Associates

(57) ABSTRACT

A guiding apparatus M comprises a stopper 30 for restricting the depth of insertion of a sheath 10. The sheath 10 is slidingly movably inserting into the stopper 30. Moreover, a lock bar 40, which is generally in orthogonal relation to the sheath 10, is received in the stopper 30. One end portion of the lock bar 40 projects from the stopper 30 and serves as a control portion 41, while the other end portion thereof is provided with slits 42a and serves as a biasing portion 42. A recess 43 for partly receiving therein the sheath 10 is formed in an intermediate section of the lock bar 40. An inner surface of the recess 43 is urged against an outer periphery of the sheath 10 under the effect of the biasing portion 42, thereby locking the stopper 30 to the sheath 10. By pressing the control portion 41 against the force of the biasing portion 42, the stopper 30 is unlocked.

7 Claims, 4 Drawing Sheets

SURGICAL OPERATION GUIDING APPARATUS

BACKGROUND OF THE INVENTION

This invention relates to an apparatus used for guiding an instrument in a surgical operation such as a brain surgical operation.

For example, in a surgical operation for removing a hematoma from a brain, various surgical instruments such as an endoscope and a suction tube for sucking blood are inserted into the brain through a hole formed in the skull of a patient. A typical guiding apparatus for guiding the endoscope, the suction tube, etc. generally comprises a sheath for allowing passage of those surgical instruments, and a mandrel. The mandrel is used when the sheath is inserted into the brain. A distal end portion of the mandrel is rounded and projected from a distal end of the sheath so that it will not damage the brain when the sheath is inserted into the brain. After the distal end portion-of the mandrel reaches the hematoma, the mandrel is withdrawn and the endoscope and the suction tube are inserted into the sheath.

With this conventional construction, an assistant to the surgeon must keep holding the sheath while maintaining a proper depth and angle of insertion into the brain (body) during the time the surgeon performs an operation using the endoscope and the suction tube. This imposes a great burden on the assistant.

Japanese Unexamined Patent Publication (Kokai) No. Hei 9-154803 discloses a guiding apparatus including a transparent sheath but it does not disclose any means for restricting the depth of insertion of the sheath.

SUMMARY OF THE INVENTION

It is an object of the present invention to provide a guiding apparatus capable of properly restricting the depth of insertion of a sheath into the body of a patient.

In order to achieve the above object, a stopper for limiting the depth of insertion of a sheath of a guiding apparatus into the body of a patient is disposed on an outer periphery of the sheath. This stopper is capable of displacing the sheath in an axial direction. In the case where the guiding apparatus is used for a brain operation, the stopper is brought into abutment with the skull of the patient.

Preferably, the stopper is slidably supported by the sheath and a lock mechanism is disposed on the stopper. This lock mechanism releasably locks the stopper to the sheath.

More preferably, a first hole and a second hole are formed in the stopper. The first hole is in the form of a through-hole and a second hole has a closed end and an open end. The first and second holes are generally in orthogonal relation with their axes offset and they are in communication with each other at their intermediate sections. The sheath is slidably inserted into the first hole and a lock member is slidably inserted into the second hole. A recess is formed in that area of the lock member which faces the first hole. The sheath is partly received in the recess. One end portion of the lock member projects from the open end of the second hole and serves as a control portion. Biasing means is received in the closed end of the second hole. The biasing means biases the lock member so as to urge a surface of the recess against an outer peripheral surface of the sheath so that the sheath is locked. The urged state of the lock member against the sheath is released by a force applied to the control portion against the effect of the biasing means. Consequently, the locked state of the sheath is released, too.

DETAILED DESCRIPTION OF THE EMBODIMENTS

Figure 1:
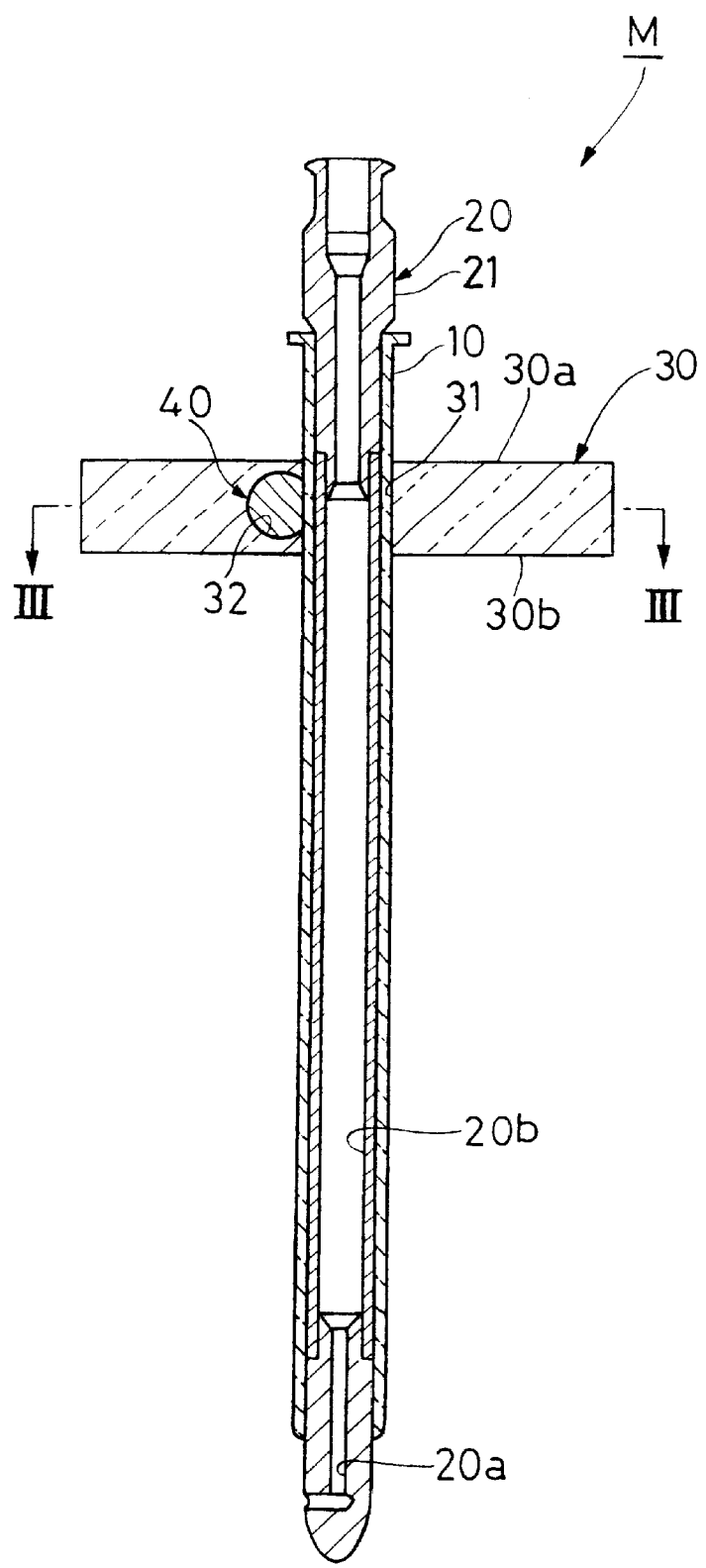
FIG. 1 is a vertical sectional view of a guiding apparatus according to a first embodiment of the present invention.
Figure 2:
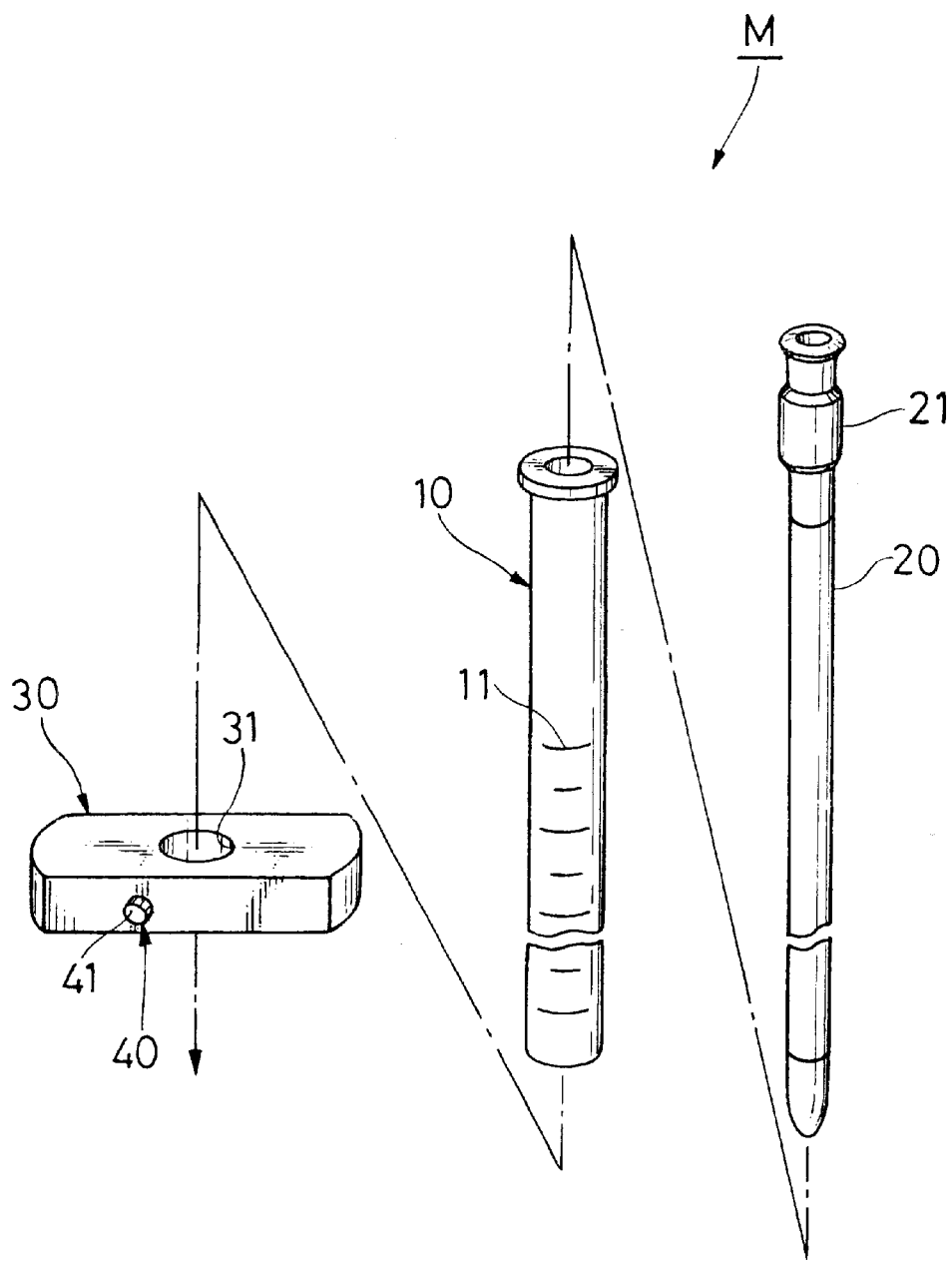
FIG. 2 is an exploded perspective view of the above apparatus.

Embodiments of the present invention will be described hereinafter with reference to the drawings. FIGS. 1 and 2 show a guiding apparatus M according to a first embodiment of the present invention. The apparatus M comprises a sheath 10, a mandrel 20 capable of being inserted into and withdrawn from an interior of the sheath 10, and a stopper 30 removably attached to an outer periphery of the sheath 10.

The sheath 10 is formed in a cylindrical configuration from a transparent resin. Gradations 11 are formed on an outer peripheral surface of the sheath 10 along the axial direction. The mandrel 20 is made of metal, for example and is dimensioned longer than the sheath 10. The mandrel 20 is provided on a basal portion (upper end portion) thereof with an engagement portion 21 of an enlarged diameter. This engagement portion 21 is abutted with a basal end (upper end) of the sheath 10 thereby positioning the mandrel 20 with respect to the sheath 10. A distal end portion (lower end portion) of the mandrel 20 thus positioned projects from a distal end (lower end) of the sheath 10. The mandrel 20 is of a cylindrical configuration and its distal end portion is rounded. A hole 20a is open in an outer periphery of the distal end portion of the mandrel 20. The hole 20a is in communication with an internal space 20b of the mandrel 20.

The stopper 30 is formed in a plate-like configuration from a transparent resin. The stopper 30 is attached to an outer periphery of the sheath 10 in order to restrict the depth of insertion of the sheath 10 into the body. A lower surface 30b out of upper and lower flat surfaces 30a, 30b of the stopper 30 serves as an abutment surface with respect to the skull.

Figure 3:
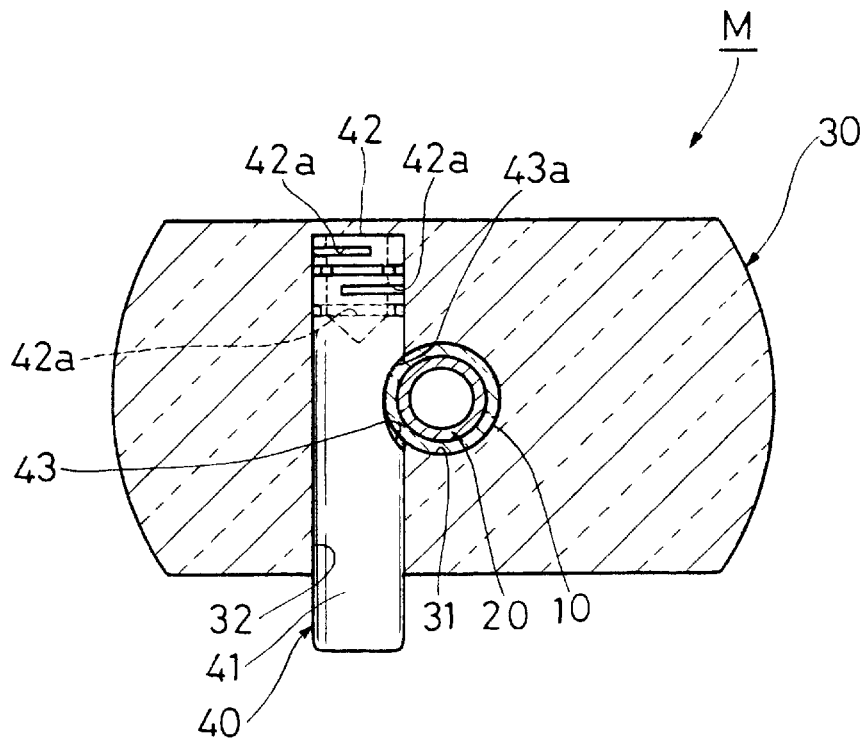
FIG. 3 is a sectional view taken on line III—III of FIG. 1.
Figure 4:
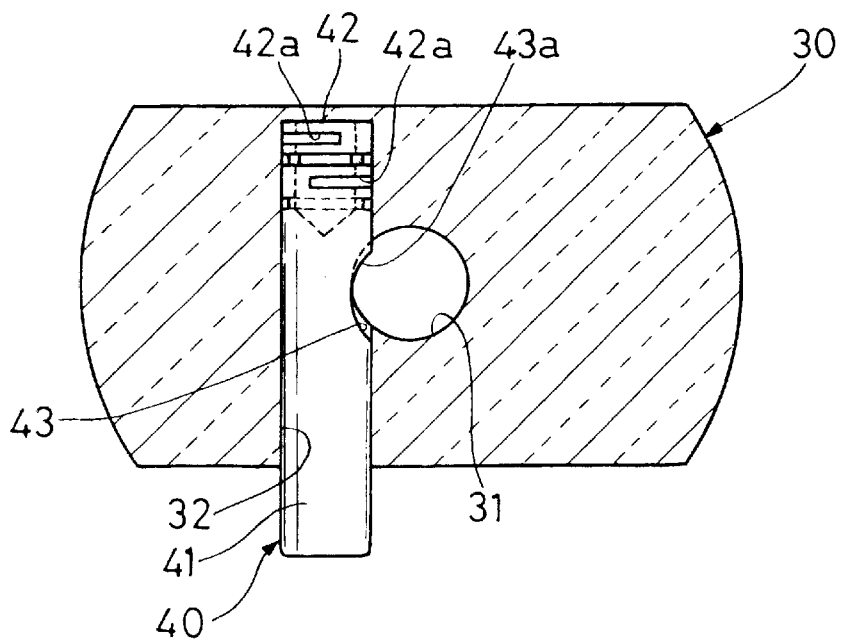
FIG. 4 is a view like FIG. 3 but in which a sheath is removed.

As best shown in FIGS. 3 and 4, the stopper 30 has a first hole 31 and a second hole 32 which are in orthogonal relation with their axes offset. The first hole 31 extends in such a manner as to be orthogonal to the flat surfaces 30a, 30b of the stopper 30. Opposite ends of the first hole 31 is open in central areas of the surfaces 30a, 30b. The second hole 32 extends in such a manner as to be parallel to the surfaces 30a, 30b. One end of the second hole 32 is closed and the other end is open in an outer peripheral surface of the stopper 30. The holes 31, 32 are in communication with each other at their intermediate sections. The sheath 10 is slidably inserted in the first hole 31. A lock bar 40 (lock member) having a circular configuration in section and extending in a direction orthogonal to the sheath 10 is slidably received in the second hole 32. An inner end portion (that end portion on the side of the closed end of the second hole 32) of the lock bar 40 is bored to have a cylindrical configuration. Four (plural) slits 42a extending in a peripheral direction are axially spacedly formed in a peripheral wall of the lock bar 40. The length of each slit 42a is about two-third of the circumference of the lock bar 40. The slits 42a are arranged such that the adjacent slits 42a are offset about 90 degrees in the peripheral direction. Owing to a provision of the slits 42a, the inner end portion of the lock bar 40 is axially elastically deformable and serves as a biasing portion 42 (biasing means) for the lock bar 40.

An outer end portion of the lock bar 40 projects from the outer peripheral surface of the stopper 30 and serves as a control portion 41 for pressing the lock bar 40. As seen, a lock mechanism, which includes the biasing portion 42 and the control portion 41, is constituted by the lock bar 40 as a single unit.

When the lock bar 40 is received in the second hole 32, its intermediate section faces the first hole 31. A recess 43 is formed in the intermediate section. The recess 43 has a cylindrical surface whose radius of curvature is slightly larger than the first hole 31.

As shown in FIG. 4, when the lock bar 40 is received in the second hole 32 of the stopper 30, a portion 43a (hereinafter referred to as the "abutment portion") of the cylindrical surface, which defines the recess 43, is located within the first hole 31 in the case where the biasing portion 42 is non-compressed and thus in a natural length. When the control portion 41 of the lock bar 40 is pressed, the biasing portion 42 is compressed and the abutment portion 43a is retracted from the first hole 31. While maintaining this condition, the sheath 10 is inserted into the first hole 31 as shown in FIG. 3. Then, when the control portion 41 is released, the abutment portion 43a is urged against the outer peripheral surface of the sheath 10 under the effect of the biasing portion 42. By this, the stopper 30 is unmovably locked to the sheath 10.

A method of use of the guiding apparatus M will now be described taking an example in which the guiding apparatus M is applied to an operation for removing a hematoma in the brain of a patient.

First, the direction and the depth from the hole bored in the skull to the hematoma is preliminarily determined using a CT, a MRI or the like. Then, the control portion 41 of the lock bar 40 is pressed to slightly compress the biasing portion 42 so that the urging state of the abutment portion 43a of the lock bar 40 against the outer peripheral surface of the sheath 10 is canceled, thereby canceling the locked state of the stopper 30. Then, the stopper 30 is slidingly moved in the axial direction of the sheath 10 so that it is matched with the gradation 11 corresponding to the depth to the hematoma. Then, the control portion 41 is released to lock the stopper 30 to the sheath 10.

Subsequently, the mandrel 20 is inserted into the sheath 10. With the distal end portion of the mandrel 20 projected from the distal end of the sheath 10, the sheath 10 and the mandrel 20 are inserted into the hole of the skull in that direction which has been determined using the CT or the like. When the apparatus M is inserted until the abutment surface 30b of the stopper 30 hits the skull, the distal end portion of the mandrel 20 reaches the hematoma.

In the case where the viscosity of the hematoma is low and the blood pressure is high, blood enters the hole 20a of the mandrel 20 and comes out of an opening formed in the basal end portion of the mandrel 20 through the internal space 20b when the distal end portion of the mandrel 20 reaches the hematoma. By this, it can be recognized that the apparatus has reached the hematoma. Should no blood come out, an injector may be inserted into the mandrel 20 to check whether blood is drawn therein and if blood is drawn therein, it can be recognized that the apparatus has reached the hematoma. After the recognition, the mandrel 20 is withdrawn from the sheath 10. Then, an observation and treatment instrument is inserted into the sheath 10. That is to say, such surgical treatments are performed that the hematoma is suckingly removed by the suction tube and the diseased part is coagulated by a laser fiber while observing it through the endoscope. Since those instruments are known, illustration thereof is omitted. As to the type of the endoscope, reference is made to FIG. 5. Since the sheath 10 is transparent, the outside of the sheath 10 can also be observed by the endoscope.

During the time an operation made by the surgeon is undergoing, the assistant to the surgeon keeps the stopper 30 in abutment with the skull. By doing so, a standstill state of the sheath 10 can easily be maintained and therefore, it can be positively prevented that the sheath 10 is inadvertently inserted deeper. This reduces the burden on the assistant and thus, reliability of the operation is enhanced.

Moreover, the sheath 10 can rapidly be adjusted in depth and angle in the state in which the sheath 10 is inserted in the brain. Specifically, in the case where a shallower area is to be treated, the sheath 10 is retracted in the withdrawing direction. Since this causes the stopper 30 to be brought away from the skull, the control portion 41 is pressed to cancel the locked state of the stopper 30 so that the stopper 30 is slidingly moved towards the distal end of the sheath 10. Then, after the stopper 30 is abutted with the skull again, the control portion 41 is released to lock the stopper 30 again. On the other hand, in the case where a deeper area is to be treated, the control portion 41 is pressed to cancel the locked state of the stopper 30. Then, the sheath 10 is inserted deeper. Thereafter, the control portion 41 is released to lock the stopper 30 again. Moreover, by inclining the sheath 10 in a range of a solid angle of about 30 degree with the stopper 30 abutted with the skull, the distal end position of the sheath 10 can be adjusted.

Figure 5:
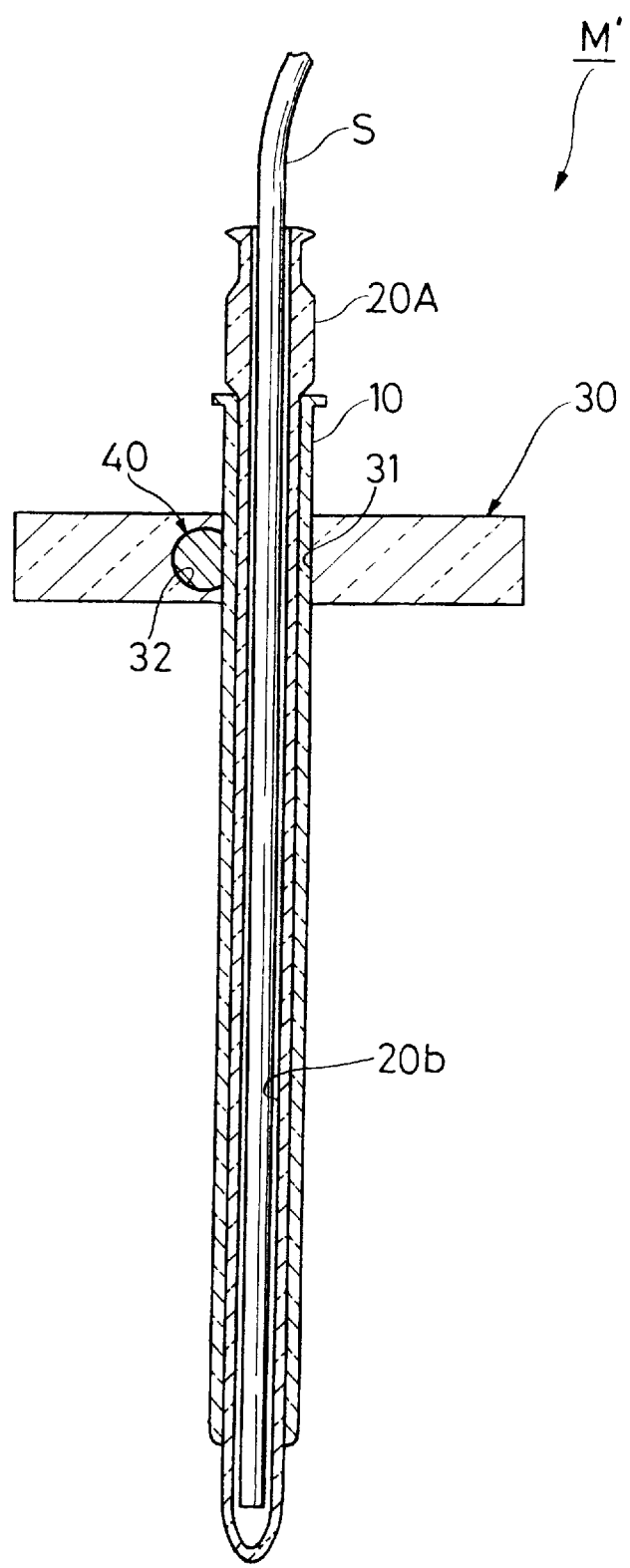
FIG. 5 is a vertical sectional view of a guiding apparatus according to a second embodiment of the present invention.

Next, a guiding apparatus M' according to a second embodiment of the present invention will be described with reference to FIG. 5. In the apparatus M', the constitution common to the guiding apparatus according to the first embodiment is denoted by identical reference numeral and description thereof is omitted.

The guiding apparatus M' is different from the first embodiment only in a mandrel 20A. The mandrel 20A is formed in a cylindrical configuration from a transparent resin and its rounded distal end is closed.

For insertion of the guiding apparatus M' into the body of a patient, an endoscope S is preliminarily inserted into an internal space 20b of a mandrel 20A. Since both the sheath 10 and the mandrel 20A are transparent, the view field of the endoscope S is never interfered by the sheath 10 and the mandrel 20A. By this, it can positively be recognized whether the distal end portion of the mandrel 20A has reached the hematoma while observing through the endoscope S.

It should be noted that the present invention is not limited to the above embodiments but that various modifications can be made. For example, the slits formed in the biasing portion of the lock bar may be spiral. Moreover, the means for biasing the lock bar may be a coiled spring, a rubber material or the like, which is separately situated from the lock bar. The stopper may be a pair of clamping member for clampingly holding the sheath.

What is claimed is:

1. A surgical operation guiding apparatus comprising:
   a) a sheath for allowing passage of an instrument inserted into a body of a patient;

b) a stopper for limiting the depth of insertion of said sheath into the body, said stopper being attached to an outer periphery of said sheath such that said sheath can be displaced in an axial direction;

c) said stopper being slidingly movably supported by said sheath and a lock mechanism being disposed on said stopper, said lock mechanism releasably locking said stopper to said sheath; and d) said lock mechanism including a lock member received in said stopper and biasing means for urging said lock member against an outer peripheral surface of said sheath, that portion of said lock member, which projects from an outer surface of said stopper, being provided as a control portion, the urged state of said lock member against said sheath being canceled by force applied to said control portion against the effect of said biasing means.

2. A surgical operation guiding apparatus according to claim 1, wherein said stopper is formed therein with a first hole in the form of a through-hole and a second hole whose one end is closed and the other end is open, said first and second holes are generally in orthogonal relation with their axes offset and in communication with each other at their intermediate sections, said sheath is slidably inserted into said first hole and said lock member is slidably inserted into said second hole, a recess is formed in that area of said lock member which faces said first hole, said sheath is partly received in said recess, and one end portion of said lock member projects from the open end of said second hole and serves as said control portion, said biasing means is received in the closed end of said second hole, and said biasing means biases said lock member to urge a surface of said recess against an outer peripheral surface of said sheath.

3. A surgical operation guiding apparatus according to claim 2, wherein said lock member includes a lock bar, a plurality of slits extending in a peripheral direction are formed in an end portion of said lock bar, thereby the inner end portion of said lock bar is axially elastically deformable and serves as said biasing means.

4. A surgical operation guiding apparatus according to claim 1, wherein said guiding apparatus is constituted such that it can be used for a brain operation, said stopper includes an abutment surface which can be abutted with the skull of a patient, and said sheath projects from said abutment surface.

5. A surgical operation guiding apparatus according to claim 1, wherein said sheath is provided with gradations along an axis thereof.

6. A surgical operation guiding apparatus according to claim 1, further comprising a mandrel, said mandrel is inserted into said sheath when said sheath is inserted into the body of a patient, a distal end portion of said mandrel is rounded and projects from a distal end of said sheath.

7. A surgical operation guiding apparatus according to claim 6, wherein said sheath and mandrel are transparent, and said mandrel has a cylindrical configuration, whose distal end portion is closed.

* * * * *